US00PP34732P2

(12) United States Plant Patent
Miyazaki

(10) Patent No.: US PP34,732 P2
(45) Date of Patent: Nov. 8, 2022

(54) ***SENECIO* PLANT NAMED 'SENE NIREGOKU'**

(50) Latin Name: *Senecio cruentus*
Varietal Denomination: Sene Niregoku

(71) Applicant: Kiyoshi Miyazaki, Shiga (JP)

(72) Inventor: Kiyoshi Miyazaki, Shiga (JP)

(73) Assignee: SUNTORY FLOWERS LIMITED, Tokyo (JP)

( * ) Notice: Subject to any disclaimer, the term of this patent is extended or adjusted under 35 U.S.C. 154(b) by 0 days.

(21) Appl. No.: 17/738,650

(22) Filed: May 6, 2022

(51) Int. Cl.
*A01H 5/02* (2018.01)
*A01H 6/14* (2018.01)

(52) U.S. Cl.
USPC ..... Plt./480
CPC ..... *A01H 6/14* (2018.05)

(58) Field of Classification Search
USPC ..... Plt./480
CPC ..... A01H 6/14; A01H 5/02
See application file for complete search history.

*Primary Examiner* — Keith O. Robinson
(74) *Attorney, Agent, or Firm* — C. Anne Whealy

(57) ABSTRACT

A new and distinct cultivar of *Senecio* plant named 'Sene Niregoku', characterized by its upright and uniformly mounded plant habit; vigorous growth habit; freely branching habit; early and freely flowering habit; and daisy-type inflorescences with ray florets that are white in color with dark purplish red-colored apices.

1 Drawing Sheet

Figure 1:
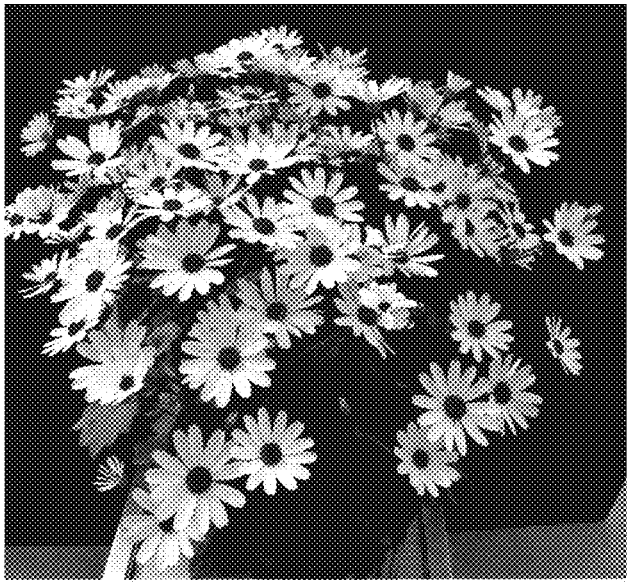

Botanical designation: *Senecio cruentus.*
Cultivar denomination: 'SENE NIREGOKU'.

STATEMENT REGARDING PRIOR DISCLOSURES BY THE INVENTOR & APPLICANT/ASSIGNEE

The Inventor and Inventor/Applicant and Assignee, Suntory Flowers Limited of Tokyo, Japan, assert that no publications nor advertisements relating to sales, offers for sale or public distribution occurred more than one year prior to the effective filing date of this application. Any information about the claimed plant would have been obtained from a direct or indirect disclosure from the Inventor/Applicant and/or Assignee. Inventor/Applicant and Assignee claim a prior art exception under 35 U.S.C. 102(b)(1) for disclosure and/or sales prior to the filing date but less than one year prior to the effective filing date.

BACKGROUND OF THE INVENTION

The present invention relates to a new and distinct cultivar of *Senecio* plant, botanically known as *Senecio cruentus*, and hereinafter referred to by the name 'Sene Niregoku'.

The new *Senecio* plant is a product of a planned breeding program conducted by the Inventor in Higashiomi, Shiga, Japan. The objective of the breeding program is to create new upright, uniformly mounding and vigorous *Senecio* plants with a freely-branching habit, early flowering and numerous attractive inflorescences.

The new *Senecio* plant originated from a cross-pollination conducted by the Inventor in March, 2016 of a proprietary selection of *Senecio cruentus* identified as code designation S12-78-Tb1 , not patented, as the female, or seed, parent with a proprietary selection of *Senecio cruentus* identified as code designation S12-106A-7, not patented, as the male, or pollen, parent. The new *Senecio* plant was discovered and selected by the Inventor as a single flowering plant within the progeny of the stated cross-pollination in a controlled greenhouse environment in Higashiomi, Shiga, Japan in February, 2017.

Asexual reproduction of the new *Senecio* plant by terminal vegetative cuttings in a controlled greenhouse environment in Higashiomi, Shiga, Japan since October, 2018 has shown that the unique features of this new *Senecio* plant are stable and reproduced true to type in successive generations.

SUMMARY OF THE INVENTION

Plants of the new *Senecio* have not been observed under all possible combinations of environmental conditions and cultural practices. The phenotype may vary somewhat with variations in environmental conditions such as temperature and light intensity, without, however, any variance in genotype.

The following traits have been repeatedly observed and are determined to be the unique characteristics of 'Sene Niregoku'. These characteristics in combination distinguish 'Sene Niregoku' as a new and distinct *Senecio* plant:

1. Upright and uniformly mounded plant habit.
2. Vigorous growth habit.
3. Freely branching habit.
4. Early and freely flowering habit.
5. Daisy-type inflorescences with ray florets that are white in color with dark purplish red-colored apices.

Plants of the new *Senecio* can be compared to plants of the female parent selection. Plants of the new *Senecio* differ primarily from plants of the female parent selection in disc floret color as plants of the new *Senecio* have purplish red-colored disc florets whereas plants of the female parent selection have deep blue-colored disc florets.

Plants of the new *Senecio* can be compared to plants of the male parent selection. Plants of the new *Senecio* differ primarily from plants of the male parent selection in disc floret color as plants of the new *Senecio* have purplish red-colored disc florets whereas plants of the male parent selection have deep blue-colored disc florets. In addition, plants of the new *Senecio* flower earlier than plants of the male parent selection.

Plants of the new *Senecio* can also be compared to plants of *Senecio cruentus* 'Sene Gosigore', disclosed in U.S. Plant Pat. No. 31,255. In side-by-side comparisons, plants of the new *Senecio* differ from plants of 'Sene Gosigore' in the following characteristics:

1. Plants of the new *Senecio* are taller than plants of 'Sene Gosigore'.
2. Plants of the new *Senecio* are more freely branching than plants of 'Sene Gosigore'.
3. Plants of the new *Senecio* flower earlier than plants of 'Sene Gosigore'.
4. Plants of the new *Senecio* have smaller inflorescences than plants of 'Sene Gosigore'.
5. Ray florets of plants of the new *Senecio* are white in color with dark purplish red-colored apices whereas ray florets of plants of 'Sene Gosigore' are solid white in color.
6. Disc florets of plants of the new *Senecio* are purplish red in color whereas disc florets of plants of 'Sene Gosigore' are violet blue in color.

BRIEF DESCRIPTION OF THE PHOTOGRAPHS

The accompanying photographs illustrate the overall appearance of the new *Senecio* plant showing the colors as true as it is reasonably possible to obtain in colored reproductions of this type. Colors in the photographs may differ slightly from the color values cited in the detailed botanical description which accurately describe the colors of the new *Senecio* plant.

The photograph at the top of the photographic sheet (FIG. 1) is a side perspective view of a typical flowering plant of 'Sene Niregoku' grown in a container.

Figure 2:
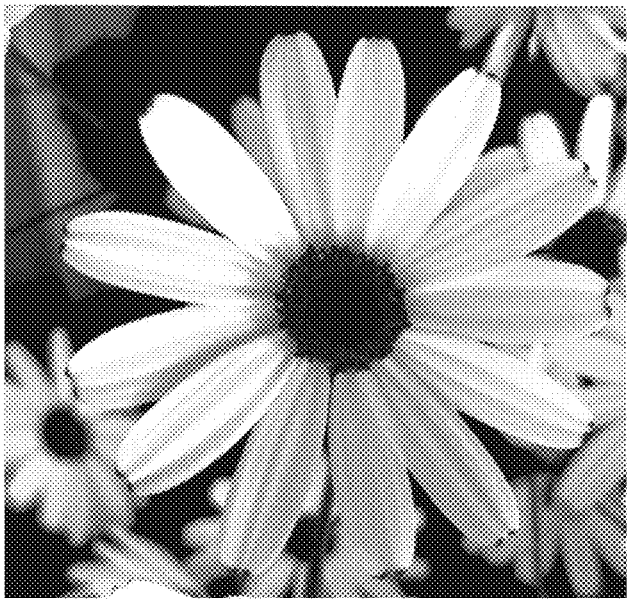

The photograph at the bottom of the photographic sheet (FIG. 2) is a close-up view of a typical inflorescence of 'Sene Niregoku'.

DETAILED BOTANICAL DESCRIPTION

The aforementioned photographs, following observations and measurements describe plants grown during the spring in 24-cm containers in an outdoor nursery in Higashiomi, Shiga, Japan and under cultural practices typical of commercial *Senecio* production. During the production of the plants, day temperatures averaged 10° C. and night temperatures averaged 5° C. Measurements and numerical values represent averages for typical flowering plants. Plants were six months old when the photographs and the detailed description were taken. In the following description, color references are made to The Royal Horticultural Society Colour Chart, 2015 Edition, except where general terms of ordinary dictionary significance are used.

Botanical classification: *Senecio cruentus* 'Sene Niregoku'.

Parentage:

*Female, or seed, parent*.—Proprietary selection of *Senecio cruentus* identified as code designation S12-78-Tb1, not patented.

*Male, or pollen, parent*.—Proprietary selection of *Senecio cruentus* identified as code designation S12-106A-7, not patented.

Propagation:

*Type*.—Terminal vegetative cuttings.

*Time to initiate roots, summer and winter*.—About one week at temperatures about 18° C. to 20° C.

*Time to produce a rooted young plant, summer and winter*.—About four weeks at temperatures about 18° C. to 20° C.

*Root description*.—Fine, fibrous; typically white in color, actual color of the roots is dependent on substrate composition, water quality, fertilizer type and formulation, substrate temperature and physiological age of roots.

*Rooting habit*.—Freely branching.

Plant description:

*Plant form and growth habit*.—Upright and uniformly mounded plant habit; daisy-type inflorescences positioned above the foliar plane; vigorous growth habit; freely branching habit with about eight primary branches each with numerous secondary branches.

*Plant height*.—About 36.3 cm.

*Plant diameter*.—About 43 cm.

*Lateral branches*.—Length: About 20 cm. Diameter: About 4.1 mm. Internode length: About 3.2 cm. Strength: Strong. Aspect: Mostly upright. Texture: Smooth, glabrous. Color: Close to 144B.

*Leaf description*.—Arrangement: Alternate, simple. Length: About 6.4 cm. Width: About 7.7 cm. Shape: Cordate. Apex: Acute. Base: Cordate. Margin: Crenate to serrate; moderately undulate. Texture and luster, upper surface: Sparsely pubescent; matte. Texture and luster, lower surface: Densely pubescent, rough; matte. Venation pattern: Pinnate; reticulate. Color: Developing leaves, upper surface: Close to 137A. Developing leaves, lower surface: Close to 138A. Fully expanded leaves, upper surface: Close to NN137B; venation, close to 144B. Fully expanded leaves, lower surface: Close to 137D; venation, close to 138C. Leaf petioles: Length: About 4.6 cm. Diameter: About 2.5 mm. Texture, upper and lower surfaces: Pubescent. Color, upper and lower surfaces: Close to 144B.

Inflorescence description:

*Appearance*.—Daisy-type inflorescences with elliptic-shaped ray florets; inflorescences arising from upper leaf axils and positioned above the foliar plane on strong peduncles; disc and ray florets developing acropetally on a capitulum; inflorescences face mostly upright to slightly outwardly; freely flowering habit with about 84 inflorescences developing per plant.

*Fragrance*.—Moderately fragrant, pleasant.

*Natural flowering season*.—Early flowering habit; plants of the new *Senecio* begin flowering about 22 weeks after planting; plants flower continuously from winter to late spring in Japan.

*Inflorescence longevity*.—Inflorescences last about two weeks on the plant; inflorescences persistent.

*Inflorescence buds*.—Height: About 1.6 cm. Diameter: About 7.4 mm. Shape: Globose. Color: Close to 145C; towards the apex, close to N79B.

*Inflorescence size*.—Diameter: About 5.1 cm. Depth (height): About 1 cm. Disc diameter: About 1 cm.

*Receptacles*.—Height: About 1.5 mm. Diameter: About 6 mm. Color: Close to 139D.

*Ray florets*.—Quantity and arrangement: About 13 per inflorescence arranged in a single whorl. Length:

About 1.9 cm. Width: About 7 mm. Shape: Elliptic. Apex: Emarginate. Base: Attenuate. Margin: Entire, not undulate. Aspect: Initially upright, then horizontal; flat. Texture, upper and lower surfaces: Smooth, glabrous; velvety. Color: When opening, upper surface: Close to NN155C; towards the apex, close to N79C. When opening, lower surface: Close to 157D; towards the apex, close to N79C. Fully opened, upper surface: Close to NN155C; towards the apex, close to N79C; color does not change with subsequent development. Fully opened, lower surface: Close to NN155C; towards the apex, close to N79C; midvein, close to 145C; color does not change with subsequent development.

*Disc florets*.—Quantity per inflorescence: About 95. Length: About 8.3 mm. Diameter, at apex: About 1.6 mm. Diameter, at base: About 0.9 mm. Shape: Tubular; apex dentate, five-pointed. Texture: Smooth, glabrous. Color, immature: Proximally, close to 157C and distally, close to 71A. Color, mature: Proximally, close to 157C and distally, close to 72A.

*Phyllaries*.—Quantity and arrangement: About 13 per inflorescence arranged in a single whorl. Length: About 4.8 mm. Width: About 1.8 mm. Shape: Lanceolate. Apex: Narrowly acute. Base: Fused. Margin: Entire. Texture, upper surface: Smooth, glabrous. Texture, lower surface: Pubescent. Color, upper surface: Close to 137C. Color, lower surface: Close to 138B.

*Peduncles*.—Length: About 6.1 cm. Diameter: About 1.4 mm. Strength: Strong. Aspect: Mostly upright to outwardly. Texture: Smooth, glabrous. Color: Close to 138B.

*Reproductive organs*.—Androecium: Present on disc florets only. Filament length: About 1.2 mm. Filament color: Close to 149D. Anther size: About 1.2 mm by 1 mm. Anther shape: Narrowly ellipsoidal. Anther color: Close to 72B. Pollen amount: Abundant. Pollen color: Close to 14B. Gynoecium: Present on both ray and disc florets. Pistil length: About 6.9 mm. Stigma shape: Bi-parted. Stigma color: Close to 72B. Style color: Close to 157D. Ovary color: Close to 145C.

*Seeds and fruits*.—To date, seed and fruit development have not been observed on plants of the new *Senecio*.

Pathogen & pest resistance: To date, plants of the new *Senecio* have not been observed to be resistant to pathogens and pests common to *Senecio* plants.

Temperature tolerance: Plants of the new *Senecio* have been observed to tolerate temperatures ranging from about 0° C. to about 30° C.

It is claimed:

1. A new and distinct *Senecio* plant named 'Sene Niregoku' as illustrated and described.

* * * * *